United States Patent
Hong et al.

(10) Patent No.: US 9,616,085 B2
(45) Date of Patent: Apr. 11, 2017

(54) SIRNA HYDROGEL AND METHOD FOR MANUFACTURING THE SAME

(75) Inventors: Cheol Am Hong, Daejeon (KR); Yoon Sung Nam, Daejeon (KR); Haeshin Lee, Daejeon (KR)

(73) Assignee: KAIST IP CO., LTD. (KR)

( * ) Notice: Subject to any disclaimer, the term of this patent is extended or adjusted under 35 U.S.C. 154(b) by 0 days.

(21) Appl. No.: 13/288,167

(22) Filed: Nov. 3, 2011

(65) Prior Publication Data

US 2013/0064786 A1 Mar. 14, 2013

(30) Foreign Application Priority Data

Sep. 14, 2011 (KR) ........................ 10-2011-0092537

(51) Int. Cl.
| | |
|---|---|
| *C12N 15/11* | (2006.01) |
| *A61K 31/713* | (2006.01) |
| *A61K 38/16* | (2006.01) |
| *A61K 47/20* | (2006.01) |
| *A61K 47/24* | (2006.01) |
| *A61K 9/06* | (2006.01) |

(52) U.S. Cl.
CPC .............. *A61K 31/713* (2013.01); *A61K 9/06* (2013.01); *A61K 38/16* (2013.01); *A61K 47/20* (2013.01); *A61K 47/24* (2013.01)

(58) Field of Classification Search
None
See application file for complete search history.

(56) References Cited

U.S. PATENT DOCUMENTS

2005/0153913 A1 * 7/2005 Kosak ............................ 514/44

OTHER PUBLICATIONS

Hong et al, Gene Silencing by siRNA Microhydrogels via Polymeric Nanoscale Condensation, Aug. 2011, JACS, 133: 13914-13917.*
Mok et al, Multimeric small interfering ribonucleic acid for highly efficient sequence-specific gene silencing, published online in Jan. 2010, Nature Materials, vol. 9, pp. 272-278.*
Kim et al, Local and systemic delivery of VEGF siRNA using polyelectrolyte complex micelles for effective treatment of cancer, 2008, Journal of Controlled Release, 129: 107-116.*
Schiffelers et al, Cancer siRNA therapy by tumor selective delivery with ligand-targeted sterically stabilized nanoparticle, 2004, Nucleic Acids Res., vol. 32, No. 19, e149: 1-10.*

* cited by examiner

*Primary Examiner* — Kate Poliakova-Georgantas
(74) *Attorney, Agent, or Firm* — Nutter McClennen & Fish LLP; Isaac A. Hubner; Konstantin Linnik

(57) ABSTRACT

The present invention relates to siRNA hydrogel and a method for manufacturing the same, and more particularly, to siRNA hydrogel for targeted gene silencing, which is nano-structured for targeted gene silencing, and a method for manufacturing the same.

27 Claims, 2 Drawing Sheets

SIRNA HYDROGEL AND METHOD FOR MANUFACTURING THE SAME

CROSS-REFERENCE TO RELATED APPLICATION

This application claims priority to and the benefit of Korean Patent Application No. 10-2011-0092357 filed in the Korean Intellectual Property Office on Sep. 14, 2011, the entire contents of which are incorporated herein by reference.

TECHNICAL FIELD

The present invention relates to siRNA hydrogel and a method for manufacturing the same, and more particularly, to nano-structured siRNA hydrogel for targeted gene silencing and a method for manufacturing the same.

BACKGROUND OF THE INVENTION

In general, it is known that a small interfering RNA (hereinafter, referred to as siRNA) has a short double helix structure of 19 to 27 base pairs, which become incorporated with the RNA-induced silencing complex (RISC) and interferes with the expression of the complementary target messenger RNA (hereinafter, referred to as mRNA) in a sequence-specific manner. (Dykxhoorn, D., M. and Lieberman, J. (2006) Knocking down disease with siRNAs. Cell, 126, 231-235).

Since siRNA has an effect that precisely suppresses expression of the target mRNA even in a small amount, attempts for using siRNA for gene therapy related diseases have actively been made.

However, since siRNA is very unstable in vivo, siRNA easily degrades, and since siRNA is negatively charged in physiological condition, it cannot efficiently penetrate a cell membrane, such that it is difficult to apply siRNA for clinical uses.

In order to solve the above problems, in the related art, a method for forming a nano-sized polyelectrolyte complex by electrostatic interaction between siRNA and cationic gene carriers such as cationic peptides, lipid molecules or polymers have been used. This nanoscale complex can protect siRNA from a degrading enzyme and efficiently facilitate its translocation into a biological cell through endocytosis.

However, since siRNA has a low molecular weight (about 15,000 Dalton or less) and a short and stiff double strand structure, in order to form stable and compact polyelectrolyte complex, a strong cationic gene carrier need to be used, which causes a problem for increasing a non-specific cell toxicity.

On the other hand, a hydrogel has a network structure by forming a three dimensional crosslinking process by physically (hydrogen bond, hydrophobic interaction, and van der Waals force) or chemically (covalent bond and metal-ligand coordination) bonding water-soluble polymers. Since the hydrogel structure has a physicochemical property that is suitable for pharmaceutical applications due to high water content, the hydrogel structure has received much attention in the medical and pharmacology fields.

Accordingly, the present inventors have studied a method for using a hydrogel structure that can stably and efficiently deliver siRNA into a biological cell.

SUMMARY OF THE INVENTION

The present invention has been made in an effort to provide siRNA hydrogel for targeted gene silencing in a three dimensional network structure, which can stably and efficiently deliver a gene into a cell, and a method for manufacturing the same.

Further, the present invention has been made in an effort to provide a polyelectrolyte complex that is manufactured by electrostatic interaction between siRNA hydrogel for targeted gene silencing and a cationic gene carrier and acts as a gene therapy agent carrier, and a method for manufacturing the same.

Technical Solution

An exemplary embodiment of the present invention may provides siRNA hydrogel for targeted gene silencing having a three dimensional network structure including the following [Structural Formula 1] or the following [Structural Formula 2]:

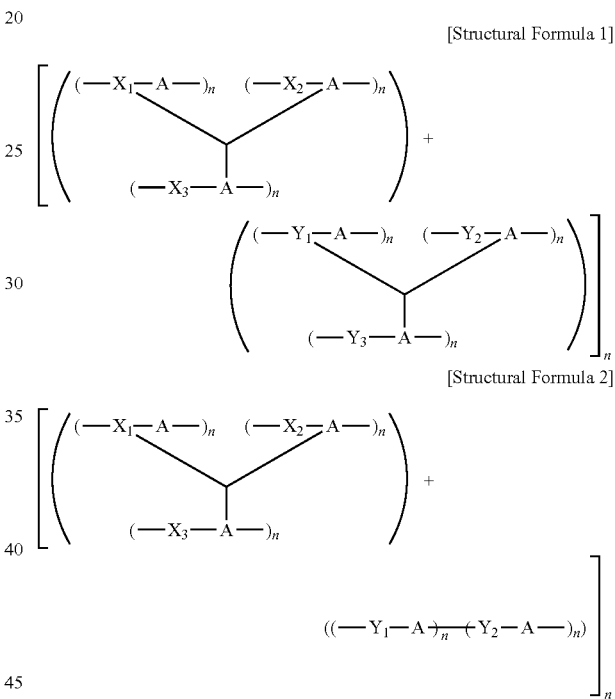

(wherein $X_1$, $X_2$ and $X_3$ are sense siRNA monomers in which the first functional group is introduced to an end, $Y_1$, $Y_2$, and $Y_3$ are antisense siRNA monomers in which the second functional group is introduced to an end, A may or may not exist, and in the case where A exists, A is a crosslinking agent or polymer, n is an integer of 1 or more).

The sense siRNA monomer and antisense siRNA monomer of [Structural Formula 1] and [Structural Formula 2] may have the number of nucleic acid bases of 13 to 60.

The first and second functional groups of Formula 1] and [Structural Formula 2] may be the same or different functional groups, and the functional groups are selected from a sulfhydryl group (—SH), a carboxyl group (—COOH), an amine group (—NH2), a hydroxy group (—OH), a formyl group (—CHO), a carbonyl group (—CO—), an ether group (—O—), an ester group (—COO—), a nitro group (—NO2), an azide group (—N3), and a sulfonic acid group (—SO3H).

The crosslinking agent of [Structural Formula 1] and [Structural Formula 2] may have a molecular weight of 100 to 10,000 Dalton, and may be one or more selected from dithio-bis-maleimidoethane (DTME), 1,8-bis-maleimidodiethyleneglycol BM(PEG)$_2$, tris-(2-maleimidoethyl)-amine (TMEA), tri-succinimidyl aminotriacetate (TSAT), 3-arm-poly(ethylene glycol) (3-arm-PEG), maleimide, N-hydroxysuccinimide (NHS), vinylsulfone, iodoacetyl, nitrophenyl azide, isocyanate, pyridyldisulfide, hydrazide, and hydroxyphenyl azide.

The polymer of [Structural Formula 1] and [Structural Formula 2] may be one or more nonionic hydrophilic polymers selected from polyethylene glycol (PEG), PLURONIC, polyvinylpyrolidone and polyoxazolin and a copolymer thereof; or one or more biodegradable polyester-based polymers selected from poly-D, L-lactic acid, poly-L-lactic acid, poly-D-lactic acid, poly-glycolic acid, poly-D lactic-co-glycolic acid, poly-L-lactic-co-glycolic acid, poly-D, L-lactic-co-glycolic acid, polycaprolactone, polyvalerolactone, polyhydroxybutyrate, polyhydroxyvalerate, and a copolymer thereof.

The siRNA hydrogel may further include a cell targeting ligand provided at an end of [Structural Formula 1] and [Structural Formula 2], wherein the cell targeting ligand may be one or more selected from a cell specific antibody, a cell targeting peptide, a gene aptamer, a cell growth factor, folic acid, galactose, mannose, RGD (arginine-glycine-aspartic acid) and transferrin.

The siRNA hydrogel for targeted gene silencing may further include a chemical coupling agent that activates the first and the second functional group of [Structural Formula 1] and [Structural Formula 2], wherein the chemical coupling agent may be one or more selected from 1-ethyl-3,3-dimethylaminopropyl carbodiimide, imidazole, N-hydroxysuccinimide, dichlorohexy carbodiimide, N-β-maleimidopropionic acid, N-β-maleimidopropylocyl succimimide ester and N-succinimidyl 3-(2-pyridyldithio) propionate.

Another exemplary embodiment of the present invention may provides a method for manufacturing siRNA hydrogel for targeted gene silencing, including: the first step for manufacturing a sense siRNA multi-conjugate by first bonding of sense siRNA monomers in which the first functional group is introduced to an end as shown in the following [Structural Formula 3]; the second step for manufacturing an antisense siRNA multi-conjugate by second bonding of antisense siRNA monomers in which the second functional group is introduced to an end as shown in the following [Structural Formula 4]; and the third step for manufacturing siRNA hydrogel of a three dimensional network structure by complementary hybridization between the sense siRNA multi-conjugate and antisense siRNA multi-conjugate:

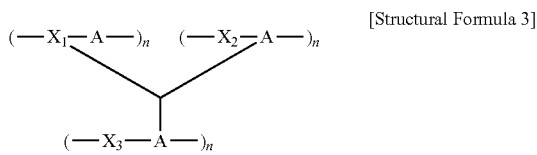

[Structural Formula 3]

(wherein $X_1$, $X_2$, and $X_3$ are sense siRNA monomers in which the first functional group is introduced to an end, A may or may not exist, and in the case where A exists, A is a crosslinking agent or polymer, n is the number of the monomers and an integer of 1 or more),

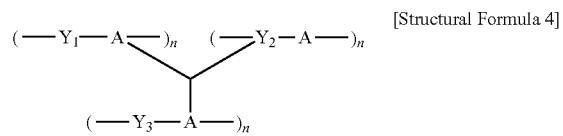

[Structural Formula 4]

(wherein $Y_1$, $Y_2$, and $Y_3$ are antisense siRNA monomers in which the second functional group is introduced to an end, A may or may not exist, and in the case where A exists, A is a crosslinking agent or polymer, n is the number of the monomers and an integer of 1 or more).

In the third step, the multi-conjugates may be prepared via complementary hydrogen bonds in the case where the sense siRNA multi-conjugate and antisense siRNA multi-conjugate are single strands, and may be direct covalent bonds, covalent bonds using the crosslinking agent as the spacer, or covalent bonds using the polymer as the spacer in the case where the sense siRNA multi-conjugate and antisense siRNA multi-conjugate form a double strand.

The covalent bonds using the crosslinking agent as the spacer or the covalent bonds using the polymer as the spacer may be one or more covalent bonds selected from an amide bond, a urethane bond; an acid-degradable ester bond, a hydrazone bond, an acetal bond; a reducing agent-degradable disulfide bond; a biodegradable bond; and an enzymatically degradable bond.

Yet another exemplary embodiment of the present invention may provides an polyelectrolyte complex including: siRNA hydrogel for targeted gene silencing according to the exemplary embodiment of the present invention; and a cationic gene carrier that is complexed with siRNA hydrogel for targeted gene silencing through electrostactic interaction, wherein the cationic gene carriers may be one or more selected from of cationic peptides, cationic lipids, and cationic polymers.

The cationic peptides may be one or more selected from KALA (cationic fusogenic peptide), polylysine, polyarginine, polyhistidine and protamine.

The cationic lipids may be one or more selected from N-[1-(2,3-dioleoyloxy)propyl]-N,N,N-trimethylammonium chloride, 1,2-dioleoyloxy-3-(trimethylammonio)propane, 1,2-dioleoyl-3-(4'-trimethyl-ammonio)butanoyl-sn-glycerol, 1,2-diacyl-3-dimethylammonium-propane, 1,2-diacyl-3-trimethylammonium-propane, 1,2-diacyl-sn-glycerol-3-ethylphosphocholin, 3β-[N—(N',N'-dimethylaminoethane)-carbamoyl]cholesterol, dimethyldioctadecylammonium bromide, and a copolymer thereof.

The cationic polymers may be one or more selected from polyethyleneimine, polyamine, polyvinylamine, poly(alkylamine hydrochloride), polyamidoamine dendrimer, diethylaminoethyl-dextran, polyvinylpyrrolidone, chitosan, and poly(2-dimethylamino)ethyl methacrylate.

Still another exemplary embodiment of the present invention may provides a method for manufacturing a polyelectrolyte complex, including: the first step for preparing siRNA hydrogel for targeted gene silencing manufactured by the method according to one exemplary embodiment of the present invention; and the second step for adding a cationic gene carrier to siRNA hydrogel for targeted gene silencing.

The charge ratio of a positive charge of the cationic gene carrier and a negative charge of siRNA hydrogel for targeted gene silencing is desirably in the range of 1:1 to 200:1.

According to the exemplary embodiments of the present invention, it is possible to alleviate or prevent a cell toxic problem generated when a strong cationic gene carrier is used through electrostatic interactions with siRNA so that siRNA has a three dimensional network structure in order to increase effective electrostatic interactions with the cationic gene carrier due to increased charge density of siRNA.

Further, since siRNA hydrogel is prepared using only siRNA molecules, it has the biocompatibility and unaffected biological function of siRNA.

DETAILED DESCRIPTION OF THE EMBODIMENTS

Figure 1:
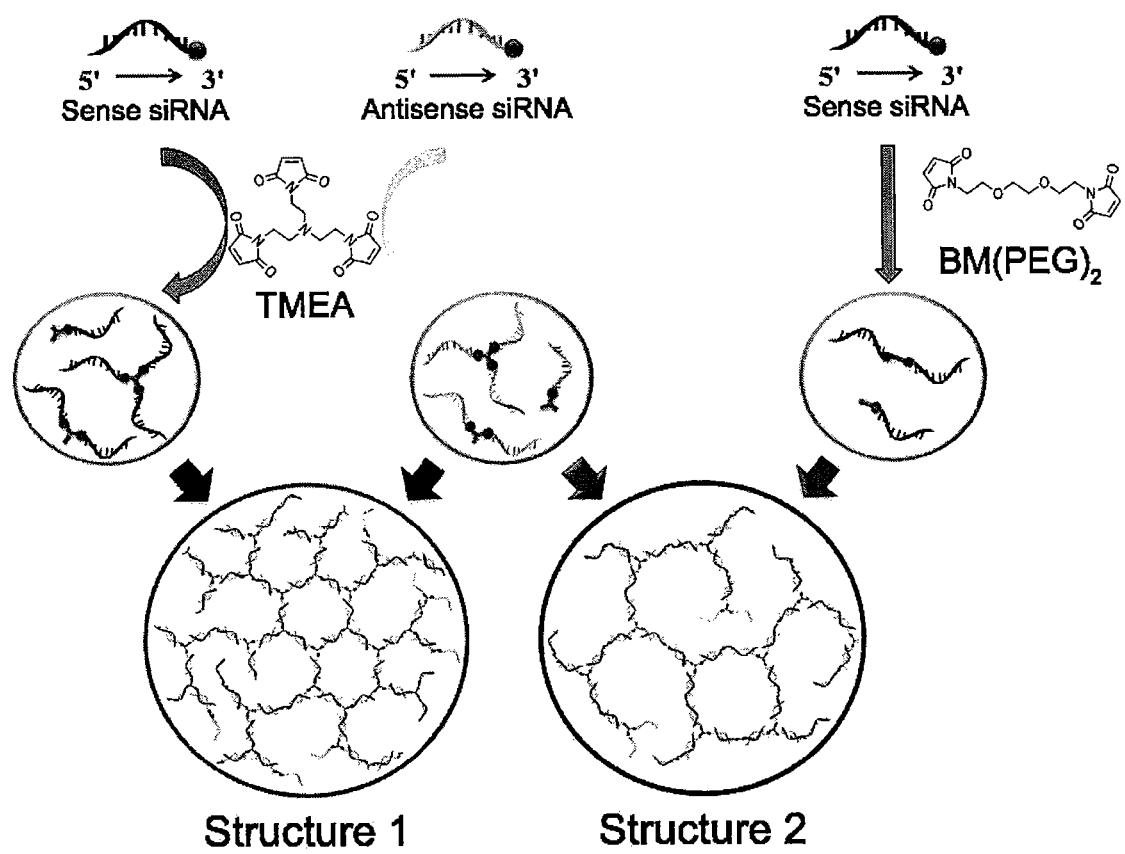
FIG. 1 is synthetic scheme for manufacturing siRNA hydrogel for targeted gene silencing according to an exemplary embodiment of the present invention.

Hereinafter, the structure and constitution of siRNA hydrogel for targeted gene silencing according to an exemplary embodiment of the present invention (hereinafter, referred to as siRNA hydrogel) will be described.

The siRNA hydrogel according to the exemplary embodiment of the present invention includes the following [Structural Formula 1] or [Structural Formula 2] and has a three dimensional network structure.

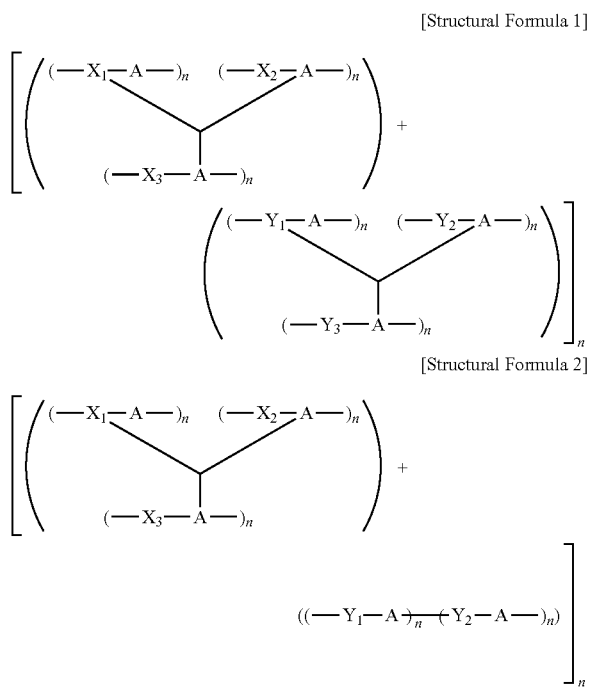

In [Structural Formula 1] and [Structural Formula 2], $X_1$, $X_2$, and $X_3$ are sense siRNA monomers in which the first functional group is introduced to an end, $Y_1$, $Y_2$, and $Y_3$ are antisense siRNA monomers in which the second functional group is introduced to an end. Further, $X_1$, $X_2$, and $X_3$ may be the antisense siRNA monomers, and $Y_1$, $Y_2$, and $Y_3$ may be the sense siRNA monomers. However, hereinafter, for convenience of description, the case where $X_1$, $X_2$, and $X_3$ are the sense siRNA monomers, and $Y_1$, $Y_2$, and $Y_3$ are the antisense siRNA monomers will be mainly described.

In [Structural Formula 1] and [Structural Formula 2], A may or may not exist, and in the case where A exists, A is a crosslinking agent or polymer. Further, n is an integer of 1 or more.

The sense siRNA monomer and antisense siRNA monomer may be constituted in a type of a single strand or a double strand, and may have the number of nucleic acid bases of 13 to 60.

Herein, siRNA is not limited to a specific kind. For example, siRNA may be c-myc, c-myb, c-fos, c-jun, bcl-2, VEGF, VEGF-B, VEGF-C, VEGF-D, or PlGF. Further, the oligo strand of siRNA may have a molecular weight of 500 to 50,000 Dalton, but not limited thereto.

In [Structural Formula 1] and [Structural Formula 2], the first functional group may be introduced into the end of the sense siRNA monomer, and the second functional group may be introduced into the end of the antisense siRNA monomer. Herein, the 'end' means 3' and/or 5' end groups of the siRNA monomer.

The first and second functional groups may be the same functional group, or different functional groups. Further, the first and second functional groups may be selected from a sulfhydryl group (—SH), a carboxyl group (—COOH), an amine group (—NH$_2$), a hydroxy group (—OH), a formyl group (—CHO), a carboxy group (—COOH), a carbonyl group (—CO—), an ether bond (—O—), an ester bond (—COO—), a nitro group (—NO$_2$), an azide (—N$_3$), and a sulfonic acid (—SO$_3$H).

A of [Structural Formula 1] and [Structural Formula 2] may or may not exist, and in the case where A does not exist, the sense siRNA monomer or antisense siRNA monomer may form a multi-conjugate through direct covalent bonds of the functional groups introduced to the ends with each other.

In the case where A is a crosslinking agent, the sense siRNA monomer or antisense siRNA monomer may form a multi-conjugate through direct covalent bonds using the crosslinking agent as a spacer. Herein, the crosslinking agent may have a molecular weight of 100 to 10,000 Dalton, and one or more selected from dithio-bis-maleimidoethane (DTME), 1,8-bis-maleimidodiethyleneglycol BM(PEG)$_2$, tris-(2-maleimidoethyl)-amine (TMEA), tri-succinimidyl aminotriacetate (TSAT), 3-arm-poly(ethylene glycol) (3-arm-PEG), maleimide, N-hydroxysuccinimide (NHS), vinylsulfone, iodoacetyl, nitrophenyl azide, isocyanate, pyridyldisulfide, hydrazide, and hydroxyphenyl azide, but is not limited thereto.

In the case where A is the polymer, the sense siRNA monomer or antisense siRNA monomer may form the multiconjugate by covalent bonds using the polymer as a spacer. Herein, the polymer may be one or more nonionic hydrophilic polymers selected from polyethylene glycol (PEG), PLURONIC, polyvinylpyrolidone, polyoxazolin, and a copolymer thereof or one or more biodegradable polyester-based polymers selected from poly-D,L-lactic acid, poly-L-lactic acid, poly-D-lactic acid, a poly-glycolic acid, poly-D-lactic-coglycolic acid, poly-L-lactic-co-glycolic acid, poly-D,L-lactic-co-glycolic acid, polycaprolactone, polyvalerolactone, polyhydroxybutyrate, polyhydroxyvalerate, and a copolymer thereof.

The siRNA hydrogel according to the exemplary embodiment of the present invention may further include cell targeting ligands provided at the ends of [Structural Formula 1] and [Structural Formula 2].

The cell targeting ligands may be introduced into the ends of [Structural Formula 1] and [Structural Formula 2] through a covalent bond such as a disulfide bond, an amide bond or an ester bond, or a non-covalent bond such as biotin-streptavidin, or a metal-ligand complex.

The cell targeting ligands may be one or more selected from a cell specific antibody, a cell selective peptide, a gene aptamer, a cell growth factor, folic acid, galactose, mannose, arginine-glycine-aspartic acid (RGD), and transferrin.

The siRNA hydrogel according to the exemplary embodiment of the present invention may further include a chemical coupling agent activating the first functional group and second functional group of [Structural Formula 1] and [Structural Formula 2].

The chemical coupling agent may be one or more selected from 1-ethyl-3,3-dimethylaminopropyl carbodiimide, imidazole, N-hydroxysuccinimide, dichlorohexylcarbodiimide, N-β-maleimidopropionic acid, N-β-maleimidopropylocyl succimimide ester, and N-succinimidyl 3-(2-pyridyldithio) propionate.

Hereinafter, a method for manufacturing siRNA hydrogel for targeted gene silencing according to the exemplary embodiment of the present invention will be described.

First Step

The method for manufacturing siRNA hydrogel for targeted gene silencing according to the exemplary embodiment of the present invention first manufactures the sense siRNA multi-conjugate by first bonding sense siRNA monomers in which the first functional group is introduced to an end as shown in the following [Structural Formula 3].

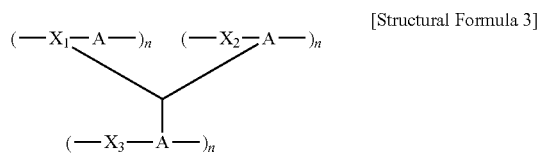

[Structural Formula 3]

In [Structural Formula 3], $X_1$, $X_2$, and $X_3$ are sense siRNA monomers in which the first functional group is introduced to the end. Since the sense siRNA monomer and first functional group are described in the above, a separate description thereof will be omitted.

In [Structural Formula 3], A may or may not exist, and in the case where A exists, A is a crosslinking agent or polymer.

In the case where A does not exist, the sense siRNA monomer may form the multi-conjugate by direct covalent bonds through the first functional group introduced to the end. Further, in the case where A is the crosslinking agent or polymer, the sense siRNA monomer may form the multi-conjugate through the covalent bonds using the crosslinking agent or polymer as the spacer. In the present specification, the direct covalent bonds of the sense siRNA monomer or the covalent bonds using the crosslinking agent or polymer as the spacer are referred to as 'first bonding'. With respect to the first bonding, the reaction temperature and time are not limited, and for example, the reaction may be performed at 5 to 60° C. for 1 to 48 hours.

The covalent bonds using the crosslinking agent or polymer as the spacer may be one or more covalent bonds selected from a non-degradable amide bond, a urethane bond; an acid-degradable ester bond, a hydrazone bond, an acetal bond; a reducing agent-degradable disulfide bond; a biodegradable bond; and an enzymatically degradable bond.

The amounts and ratio of the crosslinking agent and polymer used are not limited. The crosslinking agent and polymer may determine the size of the multi-conjugate according to the molar ratio (%) with siRNA. On the other hand, since the kinds of the crosslinking agent and polymer are described in the above, a separate description thereof will be omitted.

Finally, in [Structural Formula 3], n is the number of monomers and an integer of 1 or more.

On the other hand, the method for manufacturing siRNA hydrogel for targeted gene silencing according to the exemplary embodiment of the present invention may further include introducing a chemical coupling agent activating the first functional group introduced to the end of the sense siRNA monomer.

Since the chemical coupling agent is described in the above, a separate description thereof will be omitted (first step).

Second Step

Next, the antisense siRNA multi-conjugate is manufactured by second bonding the antisense siRNA monomer in which the second functional group is introduced to the end as shown in the following [Structural Formula 4].

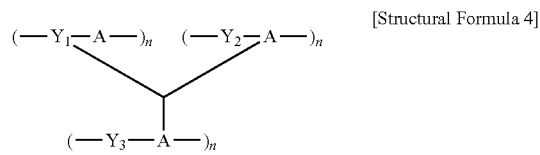

[Structural Formula 4]

In [Structural Formula 4], $Y_1$, $Y_2$, and $Y_3$ are antisense siRNA monomers in which the second functional group is introduced to the end. Since the antisense siRNA monomer and second functional group are described in the above, a separate description thereof will be omitted.

In [Structural Formula 4], A may or may not exist, and in the case where A exists, A is a crosslinking agent or polymer.

In the case where A does not exist, the antisense siRNA monomer may form the multi-conjugate by direct covalent bonds through the second functional group introduced to the end. Further, in the case where A is the crosslinking agent or polymer, the antisense siRNA monomer may form the multi-conjugate by covalent bonds using the crosslinking agent or polymer as the spacer. In the present specification, the direct covalent bonds of the antisense siRNA monomer or the covalent bonds using the crosslinking agent or polymer as the spacer are referred to as 'second bonding'. With respect to the second bonding, the reaction temperature and time are not limited, and for example, the reaction may be performed at 5 to 60° C. for 1 to 48 hours.

The covalent bonds using the crosslinking agent or polymer as the spacer may be one or more covalent bonds selected from an amide bond, a urethane bond; an acid-degradable ester bond, a hydrazone bond, an acetal bond; a reducing agent-degradable disulfide bond; a biodegradable bond; and an enzymatically degradable bond.

The amounts and ratio of crosslinking agent and polymer used are not limited. The crosslinking agent and polymer may determine the size of the multi-conjugate according to the molar ratio (%) with siRNA. On the other hand, since the kinds of crosslinking agent and polymer are described in the above, a separate description thereof will be omitted.

Finally, in [Structural Formula 4], n is the number of monomers and an integer of 1 or more.

On the other hand, the method for manufacturing siRNA hydrogel for targeted gene silencing according to the exemplary embodiment of the present invention may further include introducing a chemical coupling agent activating the second functional group introduced to the end of the antisense siRNA monomer.

Since the chemical coupling agent is described in the above, a separate description thereof will be omitted (second step).

Third Step

Next, siRNA hydrogel of the three dimensional network structure is manufactured by complementary hybridization between the sense siRNA multi-conjugate and the antisense siRNA multi-conjugate.

For example, the siRNA hydrogel may be manufactured by adding the sense siRNA multi-conjugate and antisense siRNA multi-conjugate in the same amount as each other and mixing the conjugates with a buffer solution so that the conjugates are annealed.

In this case, the conjugating of the multi-conjugates may be complementary hydrogen bonds in the case where the sense siRNA multi-conjugate and antisense siRNA multi-conjugate are single strands, and may be direct covalent bonds, covalent bonds using the crosslinking agent as the spacer, or covalent bonds using the polymer as the spacer in the case where the sense siRNA multi-conjugate and antisense siRNA multi-conjugate form a double strand.

The following solutions can be used as buffers: phosphoric acid buffer (PBS), tris buffer or HEPES buffer. Further, the salt concentration of the buffer solution may be 100 mM or more, but is not limited thereto.

The method for manufacturing siRNA hydrogel for targeted gene silencing according to the exemplary embodiment of the present invention may further include introducing a cell targeting ligand provided to the end of siRNA hydrogel.

Since the cell targeting ligand is described in the above, a separate description thereof will be omitted (third step).

As described above, since the exemplary embodiments of the present invention manufacture siRNA hydrogel using only siRNA molecules, it has the biocompatibility and unaffected biological function of siRNA, such that it is possible to be degraded by intracellular RNA enzymes to produce smaller fragments and bind to RISC for siRNA-mediated gene silencing. The present invention may provides a polyelectrolyte complex that is manufactured by electrostatic interaction between siRNA hydrogel for targeted gene silencing and cationic gene carrier and acts as a gene therapy agent carrier, and a method for manufacturing the same.

Hereinafter, a structure and constitution of a polyelectrolyte complex according to the exemplary embodiment of the present invention will be described.

The polyelectrolyte complex according to the exemplary embodiment of the present invention may include siRNA hydrogel for targeted gene silencing and the cationic gene carrier that is complexed with siRNA hydrogel for targeted gene silencing through strong electrostatic interaction.

Herein, the polyelectrolyte complex means a complex formed by electrostatic interaction between the anionic gene and the polymer having the opposite ion. The polyelectrolyte complex may have the size of 10 to 1,000 nm, and it is preferable that this complex has the size of 50 to 300 nm.

Since siRNA hydrogel for targeted gene silencing is described in the above, a separate description thereof will be omitted.

The cationic gene carriers may be one or more selected from cationic peptides, cationic lipids, and cationic polymers.

The cationic peptides may be one or more selected from KALA (cationic fusogenic peptide), polylysine, polyarginine, polyhistidine, and protamine. On the other hand, the KALA may have a peptide sequence of WEAKLAKA-LAKALAKHLAKALAKALAACEA.

The cationic lipids may be one or more selected from N-[1-(2,3-dioleoyloxy)propyl]-N,N,N-trimethylammonium chloride (DOTMA), 1,2-dioleoyloxy-3-trimethylammonio) propane (DOTAP), 1,2-dioleoyl-3-(4'-trimethyl-ammonio) butanoyl-sn-glycerol (DOTB), 1,2-diacyl-3-dimethylammonium-propane (DAP), (1,2-diacyl-3-trimethylammonium-propane (TAP), 1,2-diacyl-sn-glycerol-3-ethylphosphocholine, 3β-[N—(N',N'-dimethylaminoethane)-carbamoyl]cholesterol (DC-Cholesterol), dimethyldioctadecylammonium bromide (DDAB), and a copolymer thereof.

The cationic polymers may be one or more selected from polyethyleneimine, polyamine, polyvinylamine, poly(alkylamine hydrochloride), polyamidoamine dendrimer, diethylaminoethyl-dextran, polyvinylpyrrolidone, chitosan, and poly(2-dimethylamino)ethyl methacrylate.

Hereinafter, a method for manufacturing a polyelectrolyte complex according to the exemplary embodiment of the present invention will be described.

In the method for manufacturing the polyelectrolyte complex according to the exemplary embodiment of the present invention, first, siRNA hydrogel for targeted gene silencing (hereinafter, referred to as siRNA hydrogel) is prepared. Since the preparation of siRNA hydrogel is the same as the above, a separate description thereof will be omitted.

Next, the polyelectrolyte complex may be formed in the aqueous buffer solution, by adding siRNA to the cationic gene carrier at ambient temperature.

Since the cationic gene carrier is described in the above, a separate description thereof will be omitted. On the other hand, an addition amount of the cationic gene carrier may be determined so that a ratio of a positive charge of the cationic gene carrier and a negative charge of siRNA hydrogel is 1:1 to 200:1.

As described above, in the exemplary embodiments of the present invention, it is possible to alleviate or prevent a cell toxic problem generated when a strong cationic gene carrier is used by electrostatic interaction between siRNA hydrogel for targeted gene silencing having a three dimensional network structure and the cationic gene carrier in order to increase effective electrostatic interaction due to increased charge density of siRNA.

Hereinafter, the present invention will be described in detail through Examples. The protection scope of the present invention is not limited to the following Examples.

Example

FIG. 1 is synthetic scheme for manufacturing siRNA hydrogel for targeted gene silencing according to an exemplary embodiment of the present invention. Referring to FIG. 1, after 50 nmol of the green fluorescent protein (GFP) sense siRNA of the single strand and the antisense GFP siRNA of the single strand, in which the 3' end was substituted by the sulfhydryl group was dissolved in 1× phosphoric acid buffer solution, the 2M DTT (dithiothreitol) solution was put in order to reduce the sulfhydryl group of one end of the single strand siRNA, and the reaction was performed for about 24 hours.

If the reaction was finished, the remaining DTT was removed through the dialysis process, the solution was concentrated, TMEA (tris-(2-maleimidoethyl)-amine) that was the crosslinking agent was included in the mole number that was ⅓ of the mole number of the thiol group, and the reaction was performed at ambient temperature for 24 hours. After the reaction, the sense siRNA multi-conjugate and antisense siRNA multi-conjugate were manufactured by removing the remaining impurity such as the crosslinking agent through the dialysis process, and performing concentration. Next, siRNA hydrogel for targeted gene silencing was manufactured by adding the manufactured sense siRNA multi-conjugate and antisense siRNA multi-conjugate with the same mole number into the 1× phosphoric acid buffer solution, and performing the reaction at 5 to 60° C. for 1 hour.

Next, the prepared siRNA hydrogel was confirmed through 15% PAGE (polyacrylamide gel electrophoresis).

AFM Analysis

The Morphology and size of the three dimensional network structure of the manufactured siRNA hydrogel were observed using the AFM (atomic force microscopy). As a result of the observation, it was confirmed that since siRNA hydrogel had the three dimensional network structures, siRNA hydrogel had the high negative charge density as compared to the known siRNA.

On the other hand, the polyelectrolyte complexes were all manufactured through electrostatic interaction using the linear polyethylenimine (LPEI, molecular weight of 2,500 Dalton) at the nitrogen/phosphate (N/P) ratio of 60. If the AFM analysis image of siRNA hydrogel/LPEI complex manufactured in the exemplary embodiment of the present invention was observed, it could be confirmed that since strong electrostatic interaction with the cationic polymer efficiently increased, smaller and uniform nano-sized particles as compared to the known siRNA/LPEI complex were formed.

Measurement of the GFP (Green Fluorescence Protein) Expression Quantity.

The known siRNA/LPEI and siRNA hydrogel/LPEI complex was prepared by electrostatic interaction between siRNA suppressing the GFP gene and linear PEI (molecular weight of 2,500 Dalton) that was the cationic polymer at the N/P ration of 60. Next, after the treatment in the MDA-MB-435 cell for stably expressing the GFP that was the cancer cell for 4 hours, the GFP amount expressed after 48 hours was measured through the spectrofluorophotometer.

Figure 2:
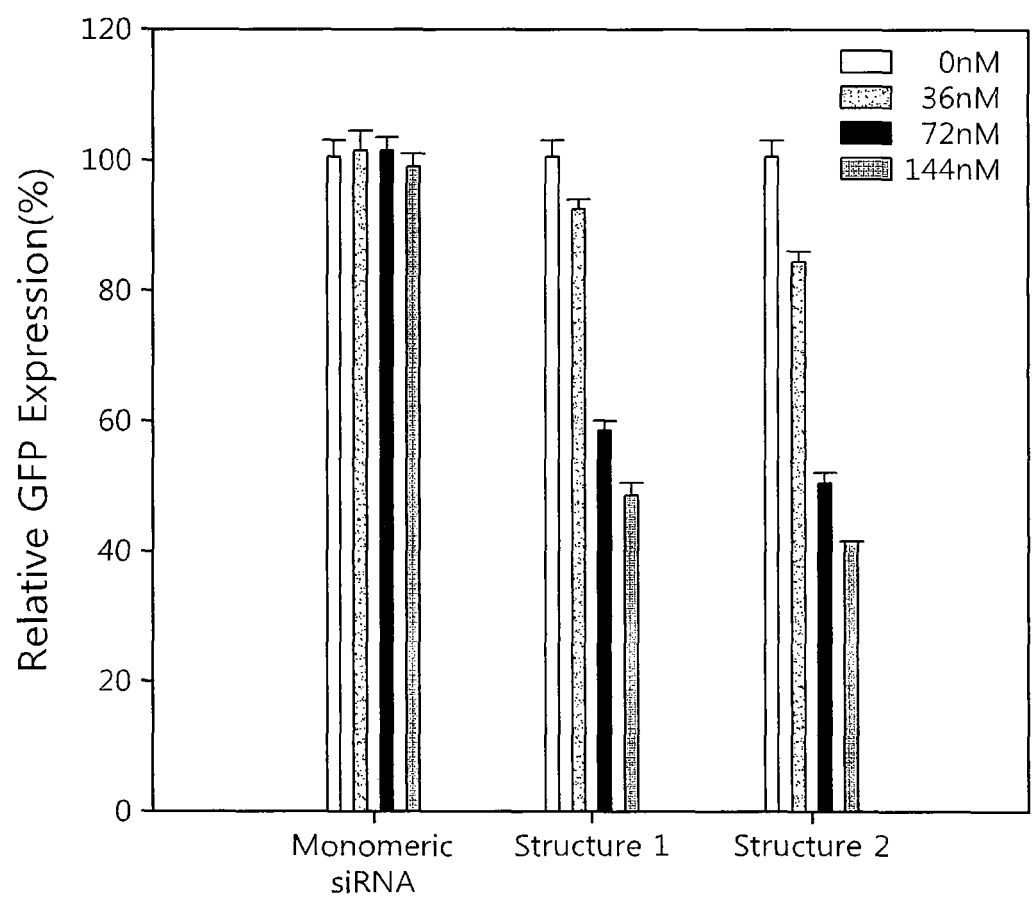
FIG. 2 is a graph illustrating a measured GFP amount.

With respect to this, FIG. 2 is a graph illustrating the measured GFP amount after the known siRNA/LPEI complex and siRNA hydrogel/LPEI complex were transfected into the MDA-MB-435 cancer cell stably expressing the GFP. In FIG. 2, A is the known siRNA/LPEI complex, and B is siRNA hydrogel/LPEI complex. As seen from the above graph, as compared to the known siRNA, siRNA hydrogel manufactured in the exemplary embodiment of the present invention has an excellent gene delivery efficiency using the cationic gene carrier, such that a targeted gene suppression effect was excellent.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. An siRNA hydrogel having a three dimensional network structure comprising pluralities of sense conjugate 1

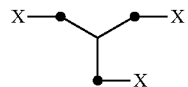

and antisense conjugate 1

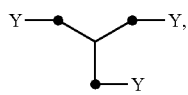

sense conjugate 1

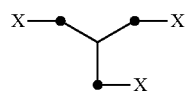

and antisense conjugate 2

or antisense conjugate 1

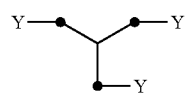

and sense conjugate 2

wherein (a) X is a sense strand of siRNA, (b) Y is an antisense strand of siRNA,

(c)

is tris-(2-maleimidoethyl)-amine (TMEA), (d) "•" is a bond formed between X or Y and

 (e)

is a linkage mediated by dithio-bis-maleimidoethane (DTME) or 1,8-bis-maleimidodiethyleneglycol BM(PEG)$_2$ between the Ys in antisense conjugate 2 or the Xs in sense conjugate 2, (f) •  and

are formed through the reaction of a functional group introduced to an end of X and Y prior to formation of • and

, wherein each of the functional groups may be the same or different, and (g) the three dimensional network structure comprises crosslinking between the plurality of sense and antisense conjugates through complementary hybridization between X and Y in adjacent sense and antisense conjugates.

2. The siRNA hydrogel according to claim 1, wherein X and Y each consist of 13-60 nucleic acid bases.

3. The siRNA hydrogel according to claim 1, further comprising:
a cell targeting ligand.

4. The siRNA hydrogel according to claim 2, wherein X and Y each consist of 19-27 nucleic acid bases.

5. The siRNA hydrogel according to claim 1, wherein each of the functional groups are a sulfhydryl group (—SH).

6. The siRNA hydrogel according to claim 5, wherein the siRNA hydrogel includes sense conjugate 1 and antisense conjugate 1.

7. The siRNA hydrogel according to claim 6, wherein the siRNA is targeted against a gene encoding green fluorescent protein (GFP).

8. The siRNA hydrogel according to claim 5, wherein the siRNA hydrogel includes sense conjugate 1 and antisense conjugate 2 or antisense conjugate 1 and sense conjugate 2.

9. The siRNA hydrogel according to claim 8, wherein o------o is a linkage mediated by BM(PEG)$_2$.

10. The siRNA hydrogel according to claim 1, wherein the siRNA hydrogel includes sense conjugate 1 and antisense conjugate 2, or antisense conjugate 1 and sense conjugate 2, and o------o is a linkage mediated by DTME.

11. The siRNA hydrogel according to claim 1, wherein the siRNA is targeted against a gene encoding GFP, c-myc, c-myb, c-fos, c-jun, bcl-2, VEGF, VEGF-B, VEGF-C, VEGF-D, or PlGF.

12. The siRNA hydrogel according to claim 11, wherein the siRNA is targeted against GFP.

13. The siRNA hydrogel according to claim 3, wherein the cell targeting ligand is selected from a cell specific antibody, a cell selective peptide, an aptamer, a cell growth factor, folic acid, galactose, mannose, arginine-glycine-aspartic acid (RGD), and transferrin.

14. The siRNA hydrogel according to claim 8, wherein o-------o is a linkage mediated by DTME.

15. The siRNA hydrogel of claim 1, wherein the sense and antisense conjugates are in equimolar amounts.

16. The siRNA hydrogel of claim 1, complexed with a cationic gene carrier, wherein the complex has a size of 10 to 1,000 nm.

17. The siRNA hydrogel of claim 15, wherein the complex has a size of 50 to 300 nm.

18. A polyelectrolyte complex comprising:
the siRNA hydrogel of claim 1; and
a cationic gene carrier comprising one or more of cationic peptides, cationic lipids, and cationic polymers and complexed with the siRNA hydrogel by electrostatic interaction.

19. The polyelectrolyte complex according to claim 18, comprising one or more cationic peptide selected from KALA (cationic fusogenic peptide), polylysine, polyarginine, polyhistidine, and protamine.

20. The polyelectrolyte complex according to claim 18, comprising one or more cationic lipid selected from N-[1-(2,3-dioleoyloxy)propyl]-N,N,N-trimethylammonium chloride, 1,2-dioleoyloxy-3-(trimethylammonio)propane, 1,2-dioleoyl-3-(4'-trimethyl-ammonio)butanoyl-sn-glycerol, 1,2-diacyl-3-dimethylammonium-propane, 1,2-diacyl-3-trimethylammonium-propane, 1,2-diacyl-sn-glycerol-3-ethylphosphocholin, 3[N—(N',N'-dimethylaminoethane)-carbamoyl]cholesterol, dimethyldioctadecylammonium bromide, and a copolymer thereof.

21. The polyelectrolyte complex according to claim 18, comprising one or more cationic polymer selected from polyethyleneimine, polyamine, polyvinylamine, poly(alkylamine hydrochloride), polyamidoamine dendrimer, diethylaminoethyl-dextran, polyvinylpyrrolidone, chitosan, and poly(2-dimethylamino)ethyl methacrylate.

22. The polyelectrolyte complex of claim 18, further comprising a cell targeting ligand.

23. A method for manufacturing the siRNA hydrogel having a three dimensional network structure of claim 1, comprising hybridizing pluralities of sense conjugate 1

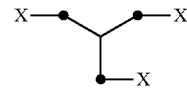

and antisense conjugate 1

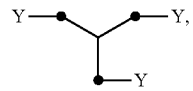

sense conjugate 1

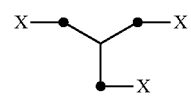

and antisense conjugate 2

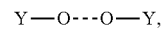

or antisense conjugate 1

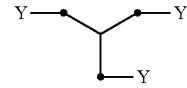

and sense conjugate 2

thereby forming the three dimensional network structure comprising crosslinking between the plurality of sense and antisense conjugates through complementary hybridization between X and Y in adjacent sense and antisense conjugates.

24. A method for manufacturing a polyelectrolyte complex, comprising: complexing the siRNA hydrogel of claim 1 and a cationic gene comprising one or more of cationic peptides, cationic lipids, and cationic polymers by electrostatic interaction.

25. The method for manufacturing a polyelectrolyte complex according to claim 24, wherein a charge ratio of a positive charge of the cationic gene carrier and a negative charge of siRNA hydro gel for targeted gene silencing is 1:1 to 200:1.

26. The method of claim 23, further comprising introducing a cell targeting ligand to the siRNA hydrogel.

27. The method of claim 24, wherein the siRNA hydrogel further comprises a cell targeting ligand.

* * * * *